US00RE34841E

United States Patent [19]

Suovaniemi et al.

[11] E Patent Number: Re. 34,841

[45] Reissued Date of Patent: Jan. 31, 1995

[54] MICRO-CUVETTE UNIT FOR FACILITATING THE IDENTIFICATION OF SAMPLES

[75] Inventors: Osmo A. Suovaniemi; Pertti Ekholm; Paul Partanen, all of Helsinki, Finland

[73] Assignee: Labsystems Oy, Helsinki, Finland

[21] Appl. No.: 951,719

[22] Filed: Sep. 25, 1992

Related U.S. Patent Documents

Reissue of:

[64] Patent No.: 4,319,841
Issued: Mar. 16, 1982
Appl. No.: 125,475
Filed: Feb. 28, 1980

[30] Foreign Application Priority Data

Mar. 1, 1979 [FI] Finland ..... 790692

[51] Int. Cl.[6] ..... G01N 21/03; C12M 1/20

[52] U.S. Cl. ..... 356/244; 356/246; 422/102; 422/104; 435/301

[58] Field of Search ..... 356/244, 246, 440; 422/102, 104; 435/301

[56] References Cited

U.S. PATENT DOCUMENTS

| | | | |
|---|---|---|---|
| 3,432,275 | 3/1969 | Unger | 356/246 |
| 3,713,985 | 1/1973 | Astle | 422/102 |
| 3,773,426 | 11/1973 | Mudd | 356/246 |
| 3,992,265 | 11/1976 | Hansen | 435/300 |
| 4,126,418 | 11/1978 | Krasnow | 356/246 |
| 4,226,531 | 10/1980 | Tiffany et al. | 356/246 |

FOREIGN PATENT DOCUMENTS

| | | |
|---|---|---|
| 1031183 | 5/1978 | Canada . |
| 2435317 | 2/1976 | Germany . |
| 2527770 | 1/1977 | Germany . |

*Primary Examiner*—Vincent P. McGraw
*Attorney, Agent, or Firm*—Hopgood, Caliamfde, Kalil & Judlowe

[57] ABSTRACT

There is disclosed a micro-cuvette unit comprising a plurality of components in the form of a matrix which is arranged so that the cuvettes may be handled as one unit. The structural body of the micro-cuvette unit comprises a rectangular frame which is designed so that a plurality of cuvette components may be fitted to the frame, one after another. Each cuvette component comprises a plurality of cuvettes arranged in the form of a line or matrix and connected to each other directly or by means of support discs. The frame part of the micro-cuvette unit is open in the middle, at least within the area covered by the cuvettes in the cuvette components. The frame part contains two opposite sides which are provided with connecting means for joining the cuvette components to the frame part. These connecting means are different on different sides of the frame part and on different sides of the cuvette components so that their positions in relationship to each other may be readily determined and so that the identification of samples may be facilitated.

9 Claims, 1 Drawing Sheet

MICRO-CUVETTE UNIT FOR FACILITATING THE IDENTIFICATION OF SAMPLES

Figure 1:
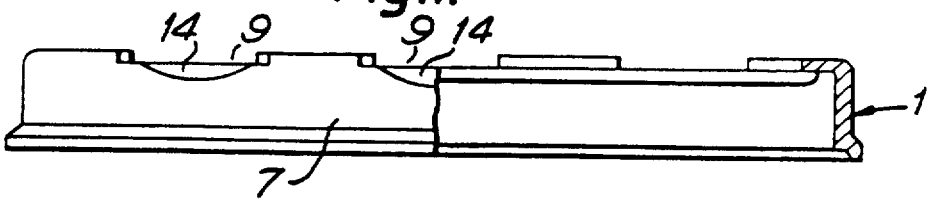

Matter enclosed in heavy brackets [ ] appears in the original patent but forms no part of this reissue specification; matter printed in italics indicates the additions made by reissue.

The subject of the present invention is a micro-cuvette unit that comprises several cuvettes in the form of a matrix as arranged so that they can be handled as one entire unit.

The micro-cuvette unit subject of the present invention can be used, e.g., for immunoassays, such as enzymeimmunoassay (EIA), hemagglutination (HA), hemagglutination inhibition (HI), complement fixation (CF), viroimmunoassay, and fluoroimmunoassay. Moreover, the unit is suitable for use in techniques and methods in which immobilized enzymes are used, as such or as combined with other methods.

Enzymeimmunoassays (EIA, ELISA, and EMIT) have replaced, e.g, radioimmunoassay methods because they are mostly sufficiently specific and sensitive for many assays. The equipment needed for them is relatively inexpensive, and mostly already existing in laboratories. The reagents are inexpensive and their storage stability is good, the handling procedures are simple, the assays rapid, and they permit automation, and therein no isotopes or isotope counters are needed.

EIA, ELISA, and EMIT are suitable for the assay of antigens, antibodies, and haptenes.

As markers are used enzymes, such as alkaline phosphatase, peroxydase, glucose-oxydase, glucose-6-phosphate-hydrogenase, etc. The antigen, antibody, and haptene enzyme conjugate needed in these assays is stable and has a long storage age.

All the EIA types (competitive EIA on antigen, immunoenzymometric assay on antigen, sandwich EIA on antigen, EIA on antibody) except homogeneous EIA (EMIT) require a process by means of which it is possible to separate fixed or free conjugate. For separation, the so-called solid phase is used to which the antigen or antibody is attached.

The microtiter plate is use is a plate of $8\times12$ matrix, in which the cuvettes are usually marked in the direction of 8 on the matrix from the right to the left from a to hand in the direction of 12 from 1 to 12. The microtiter plates of $\times12$ matrix comprise mainly three types of cuvettes: U-bottom, V-bottom and flat bottom. For the flat bottom cuvettes the abbreviation FB is used, meaning flat bottom. The most common registered microtiter plates are Cooke, Linbro, and Nunc.

Such a conventional microtiter plate is traditionally intended for HA (i.e. hemagglutination) and CF (i.e. complement fixation) techniques. A more recent form of use is cell and tissue culture on microtiter plates specifically treated for this purpose.

The uniformity of quality of conventional microtiter plates is so poor that it causes excessive variation in enzyme-immunotests. Use of the plates in optical reading by means of a photometer suitable for the purpose is unreliable, because the plates concerned do not meet the requirements of optical reading: the cuvette bottoms in the plates are subjected to scratches and dirt, and mostly they are already scratched before they are even taken to use.

Moreover, conventional microtiter plates vary from manufacturer to manufacturer in respect of their outer dimensions, as do the plates of the same manufacturer also vary in respect of their size and uniformity of quality from production batch to production bath.

Conventional microtiter plates are too large (i.e. too many cuvettes per plate). As a rule, small matrixes are needed, because the number of samples is at one time not sufficient for efficient utilisation of the entire plate. On the other hand, it should be noticed that conventional microtiter plates have an all too large quantity of rawmaterial per one cuvette.

A photometer of the type of vertical measurement and of high precision definitely requires an FB-type shape of cuvette bottom in order that optical reading may be done reliably. Moreover, the bottom window of the cuvette must definitely meet the level required by optical reading, i.e. uniformity of quality, the window's remaining uncontaminated, unscratched, and free from finger-print contamination.

The micro-cuvette unit in accordance with the invention is mainly characterized in that the structural body of the micro-cuvette unit consists preferably of a rectangular frame part, which is designed so that two or more cuvette components can be fitted to the frame one after the other, each cuvette component consisting of several cuvettes arranged in the form of line or matrix and connected to each other directly or by means of support discs and that the frame part of the micro-cuvette unit is open in the middle at least within the area covered by the cuvettes in the cuvette components.

Figure 2:
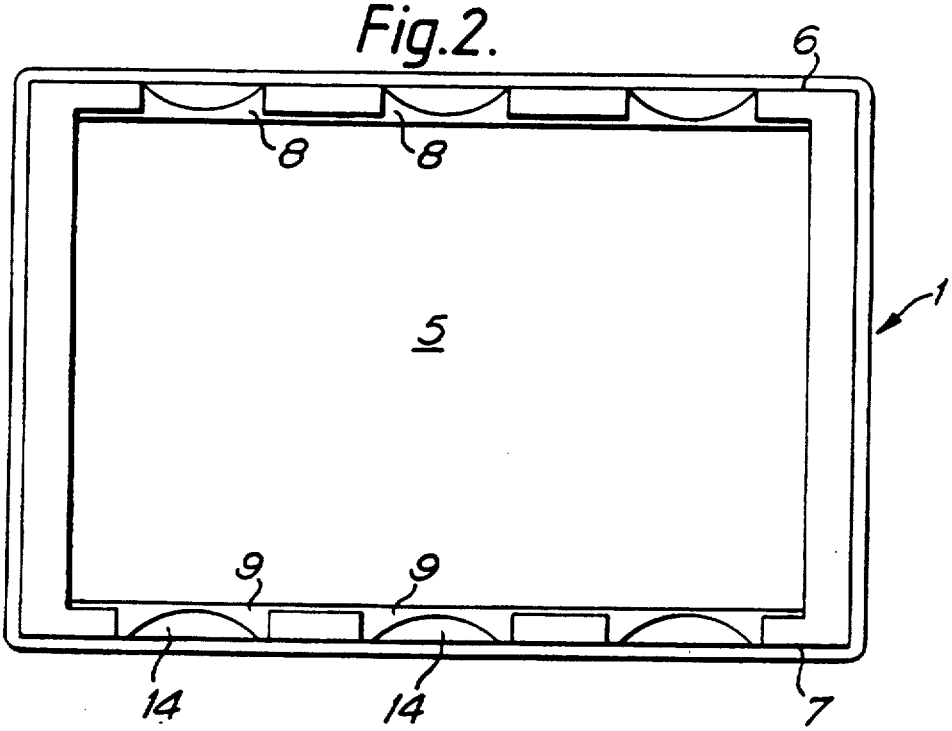
Figure 3:
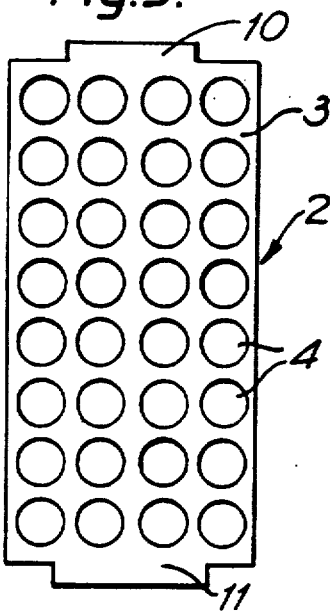
Figure 4:
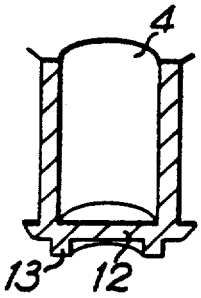
Figure 5:
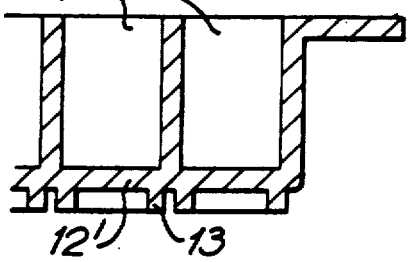

The invention is described more fully the following description and from the attached drawings, wherein FIG. 1 shows the frame part of a micro-cuvette unit in accordance with the invention as a side view and partly in section, FIG. 2 shows the frame part of the micro-cuvette unit as viewed from above, FIG. 3 shows a cuvette component intended for use with the frame part of a micro-cuvette unit, as a schematical presentation viewed from above, FIG. 4 shows a sectional perspective view of one cuvette in the cuvette component of FIG. 3, and FIG. 5 shows a construction embodiment alternative to the embodiment shown in FIG. 4, wherein two cuvettes are shown as a sectional side view.

The micro-cuvette unit in accordance with the invention consists of several parts. It comprises a rectangular frame part, whose middle part 5 is open and into which smaller units can be placed and which smaller units can be packed into this frame part 1 one after the other in line. The size of the frame part 1 is such that it suitable for being measured in a photometer. The cuvette component 2 involves the advantage of little quantity of rawmaterial per cuvette 4. The matrix size of the cuvette component 2 is smaller than $8\times12=96$, whereby it satisfies considerably more users.

Thus, the number of cuvettes 4 in the cuvette components 2 is less than 96, e.g. $4\times8=32$ or $6\times8=48$ cuvettes.

Two or more cuvette components 2 have been arranged for attachment to the frame part one after the other in line, each cuvette component 2 consisting of several cuvettes 4 in line or matrix form, said cuvettes being connected to each other by means of support discs 3.

The optical window 12 of each cuvette 4 is protected by a collar 13, whereby said window's 12 becoming scratched, dirty, or contaminated by finger prints is avoided. Moreover, it should be emphasized that it is considerably easier to manufacture cuvettes of optically higher standard if the cuvette-component matrix is smaller than 8×12, e.g. exactly 4×8 cuvettes. Study results support this opinion, for, e.g., the FP-9 cuvette component (matrix 3×3) is optically homogeneous. Moreover, it has been noticed that the passive fixation of proteins is heterogeneous (from cuvette to cuvette) in a conventional microtiter plate of matrix 8×12, wherein in a FP-9 cuvette component of matrix 3×3 this problem has not been noticed at all, but, on the contrary, the fixation is highly homogeneous from cuvette to cuvette in the same cuvette component and, moreover, from cuvette component to another cuvette component. Images of scanning-electron microscope also speak in favour of homogeneity of 3×3 FP-9 cuvette component, both as untreated (bare plastics surface) and, e.g., as coated with protein (antigen or antibody) or with any other antigen. From ordinary microtitier plates (8×12=96) it has been noticed that there are clear differences in charge between the middle areas and border areas in the plate, which may be exactly the reason for heterogeneous passive absorption on the plastics surface.

FIG. 1 shows the frame part 1 of the micro-cuvette unit as a side view. In FIG. 1, the place for the cuvette component 2 is seen as a recess 9 in the frame part 1. Moreover, e.g. in the way shown in the FIG. G., it is also possible to provide the recess 9 with a space 14 which makes it easier to raise the cuvette component 2 from, and to lower it into, the frame part 1.

In FIG. 2, the frame part 1 is shown from above, whereby it is possible to see the places for cuvette components 2, like from FIG. 1. The number of these places may be, e.g., 3, in which case the matrix size is 4×8. The number of places may equally well be 2, in which case, on the other hand, the matrix size is 6×8, or any other number whatsoever. The individual cuvette components 2 may be provided with separate codes each of them, e.g., readable mechanically and/or visually.

FIG. 3 shows a cuvette component of 4×8 matrix. From the Figure it is possible to see the narrower portions 10, 11 of different widths at different ends of the cuvette component 2, constituting indication of polarity of the cuvette component 2. This indicator of polarity makes it easier to identify the samples and, moreover, samples becoming intermixed with each other is prevented.

FIG. 4 is a sectional view of one cuvette 4 in a cuvette component 2. Each cuvette 4 is, around the optical window 12, provided with a collar 13, whose object is to protect said window.

The collar 13 protecting the optical window 12 may limit the optical window so as to be narrower than the diameter of the cuvette 4 bottom, in which case the optical window 12 is better protected from scratches and finger prints and, moreover, the collar 13 in this way formed restricts the diffused light from the light guide (e.g., fibre bundle).

FIG. 5 shows an embodiment alternative to that shown in FIG. 4, whereby the same numerals as provided with an apostrophe are used for corresponding parts. In this embodiment the cuvettes 4' are provided with a square cross-sectional form, and two adjoining cuvettes have a cuvette wall common for both of them. Of course, adjoining cuvettes with a common wall structure or part of same may also have other cross-sectional form except square.

According to a preferred method of manufacture, the cuvette components are manufactured as one piece out of plastics material so that the plastics material of the cuvette components 2 is non-transparent to the measurement light with the exception of the optical windows 12 in the bottom portions of the cuvettes 4.

What we claim is:

1. A micro-cuvette unit comprising a plurality of cuvettes in the form of [a matrix arranged] *rectangularly shaped cuvette components* so that said cuvettes may be handled as [one unit] *a unit,* wherein the structural body of the micro-cuvette unit comprises a rectangular frame part *having a rectangular opening* which is designed so that a plurality of *rectangular* cuvette components may be fitted [to] *into* said frame one after the other, each *rectangular* cuvette component comprising a plurality of cuvettes arranged in the form of a line or matrix and connected to each other directly or by means of [sufficient discs whereby] *support discs,* said *rectangular opening of said* frame part [is] *being* open in the middle *thereof* at least within the area covered by said cuvettes in said *rectangular* cuvette [components and] *components,* wherein said *rectangular* frame part contains two opposite sides which are provided with connecting means for joining said cuvette components to said frame [part] *part, and* wherein said connecting means between said frame part and said cuvette components are different on different sides of said frame part and on different sides of said cuvette components respectively so as to determine the positions of said cuvette components in relation to each other and to facilitate the identification of samples placed within said cuvettes and preventing said samples from becoming intermixed with one another.

2. The micro-cuvette unit of claim 1 wherein said unit comprises several cuvettes in the form of a matrix arranged so that they may be handled as one unit, said micro-cuvette unit comprising a rectangular frame part, designed so that two or more cuvette components may be fitted to said frame one after the other, each cuvette component comprising a plurality of cuvettes which each contain at lest one optical window in its bottom portion, said cuvette being made of a plastic material which is non-transparent to light measurement except through said optical window.

3. The micro-cuvette unit of claim 1 wherein each cuvette of said cuvette component comprises an optical window in the bottom of said cuvette, said window being protected underneath by a collar that requires said optical window to be narrower than the diameter of said cuvette bottom on order to protect said optical window from scratches and fingerprints and to restrict the diffusion of light.

*4. The micro-cuvette unit as described in claim 1, wherein said connecting means comprise said support discs on the edges of said cuvette components and recesses on said frame for receiving said support discs.*

*5. The micro-cuvette unit as described in claim 4, wherein said recesses are provided with openings to facilitate lowering or raising said cuvette components into or out of said frame.*

*6. The micro-cuvette unit as described in claim 1, wherein each cuvette unit has a separate readable code whereby identification of each cuvette unit is facilitated.*

*7. The micro-cuvette as described in claim 1, wherein said rectangular cuvette component comprises a matrix of cuvettes.*

*8. The micro-cuvette unit as described in claim 1, wherein said rectangularly shaped cuvette component is comprised of a plurality of cuvettes arranged in a line.*

*9. The micro-cuvette unit as described in claim 1, wherein each cuvette is coated with protein.*

* * * * *